(12) United States Patent
Vegh et al.

(10) Patent No.: US 7,622,597 B2
(45) Date of Patent: Nov. 24, 2009

(54) METHOD OF PREPARATION OF MALEIMIDES BY THERMAL CYCLIZATION OF MALEAMIC ACIDS IN THE PRESENCE OF A CATALYST

(75) Inventors: Zsolt Vegh, Galanta (SK); Jozef Balko, Sala (SK)

(73) Assignee: Vucht A.S., Bratislava (SK)

( * ) Notice: Subject to any disclaimer, the term of this patent is extended or adjusted under 35 U.S.C. 154(b) by 168 days.

(21) Appl. No.: 11/814,200

(22) PCT Filed: Dec. 15, 2005

(86) PCT No.: PCT/SK2005/000025

§ 371 (c)(1),
(2), (4) Date: Jul. 18, 2007

(87) PCT Pub. No.: WO2007/064306

PCT Pub. Date: Jun. 7, 2007

(65) Prior Publication Data

US 2008/0125597 A1    May 29, 2008

(30) Foreign Application Priority Data

Nov. 30, 2005    (SK) .................................. 5097-2005

(51) Int. Cl.
*C07D 207/448* (2006.01)
(52) U.S. Cl. .................... 548/548; 548/549; 562/595
(58) Field of Classification Search .................. 548/548; 562/595
See application file for complete search history.

(56) References Cited

U.S. PATENT DOCUMENTS

| 3,734,927 | A | * | 5/1973 | Kawada et al. | ............... 548/549 |
| 4,225,498 | A | * | 9/1980 | Baudouin et al. | ........... 548/435 |
| 4,851,547 | A |   | 7/1989 | Kita |  |
| 5,973,166 | A | * | 10/1999 | Mizori et al. | ............... 548/548 |
| 2003/0105337 | A1 |  | 6/2003 | Wu |  |

FOREIGN PATENT DOCUMENTS

| EP | 257831 | 3/1988 |
| EP | 415506 | 3/1991 |

* cited by examiner

*Primary Examiner*—Golam M. M. Shameem
*Assistant Examiner*—Yong Chu
(74) *Attorney, Agent, or Firm*—Oppedahl Patent Law Firm LLC

(57) ABSTRACT

Method of preparation of maleimides by thermal cyclization of maleamic acids in the presence of a catalyst consists in that reaction of a substituted maleic anhydride with a primary amine is performed in an organic solvent in the presence of betaine at a temperature of 100 to 180° C., at a ratio of the primary amine to the substituted maleic anhydride of 0.6:1.6. Maleimides, obtained in this way, are further purified by extraction, and finally, they are crystallized. As a catalyst, there may be also used betaine in a mixture with inorganic and organic acids, or betaine may be deposited on a solid carrier, or possibly, betaine may be deposited on a carrier in combination with inorganic acids.

16 Claims, No Drawings

METHOD OF PREPARATION OF MALEIMIDES BY THERMAL CYCLIZATION OF MALEAMIC ACIDS IN THE PRESENCE OF A CATALYST

TECHNICAL FIELD

Present invention concerns a method of preparation of maleimides by thermal cyclization of maleamic acids in the presence of a catalyst.

BACKGROUND ART

Compounds of maleimide type are commonly prepared in two steps. The first step includes preparation of N-substituted maleamic acid by the reaction of a primary amine with maleic anhydride. The second step is cyclodehydration of the corresponding maleamic acid to maleimide derivative.

Preparation of maleamic acid derivatives is very simple and the yields are usually nearly quantitative. It is recommended to add the corresponding primary amine gradually into the solution of maleic anhydride, which is present in the solution in equimolar ratio or in excess with respect to amine. In this way possible addition of amine on a double bond of the corresponding maleamic acid is prevented.

Cyclodehydration of maleamic acid derivatives can be performed in several ways, for example by using chemical dehydration agents like acetic acid anhydride in the presence of sodium acetate. This method is preferred in preparation of numerous aromatic maleimides at laboratory conditions (U.S. Pat. No. 2,444,536). A disadvantage of this method is the fact that industrial application is economically disadvantageous because of a great amount of acid waste waters. Moreover, there are high demands on production facilities considering the corrosive effects of acetic acid.

Direct thermal cyclodehydration of maleamic acid derivatives can be performed at a temperature of near to 200° C. This method is impractical because of polymerization of the resulting maleimide derivative at extreme conditions. Thermal cyclodehydration may be performed at lower temperatures under the conditions of azeotropic distillation in the presence of acid catalysts. The use of an azeotropic solvent facilitates effective reaction water removing from the reaction system, thus moving the reaction equilibrium in favour of the required maleimide.

Suitable azeotropic solvents are cyclohexane, benzene, ethylbenzene, xylene isomers, cumene, chlorobenzene, buthylbenzene, diethylbenzene, mesitylene and the like.

Also boiling temperature of azeotropic solvents affects the reaction rate. The use of solvents with boiling point higher than that of toluene results in reducing the reaction time, but increasing the boiling point by solvent selection may result in an increase of the amount of by-products. Whereas the use of toluene as an azeotropic dehydrating agent results in low yield and long reaction time because of low solubility of maleamic acid in the reaction medium. These disadvantages are eliminated by adding polar aprotic solvents to the reaction mixture. In the patent literature, there are claimed many polar aprotic solvents, including dimethylformamide, dimethylacetamide, acetonitrile, N-methylpyrrolidone, dimethylsulfoxide and sulfolane (U.S. Pat. No. 5,484,948, U.S. Pat. No. 5,371,236). Dimethylformamide is the most often used auxiliary solvent. A disadvantage of DMF is its unlimited miscibility with azeotropic solvent, and as a consequence, its presence in the reaction mixture complicates processing the product. Polar aprotic solvent can be removed by washing it with water, but then waste waters containing DMF arise. A further disadvantage of using DMF and dimethylacetamide is the fact, that at the reaction conditions they hydrolyze and partially decompose.

The disadvantages of polar aprotic solvents are eliminated by quaternary ammonium salts (U.S. Pat. No. 4,225,498 U.S. Pat. No. 5,973,166 JP-54-30155), which are stable and, at suitably selected temperatures, they are immiscible with azeotropic solvents and, therefore, they can be easily removed from the reaction medium. In this method, the ratio quaternary ammonium salt/acid must be kept at a certain catalytic activity. The recycled catalyst must be additionally purified and adjusted to the required ratio, thus requiring increased financial demands on the process.

DISCLOSURE OF INVENTION

The above disadvantages are eliminated by a method of maleimide preparation by thermal cyclization of maleamic acids in the presence of a catalyst according to the present invention, the subject matter of which consists in that the reaction of a substituted maleic anhydride and primary amine is performed in an organic solvent in the presence of betaine at a temperature of 100 to 180° C., whereby the ratio of the primary amine to the substituted maleic anhydride is 0.6-1.6, and it is preferred, if the molar ratio of betaine to the primary amine is 0.01-1.2. Maleimides, obtained in this way, are further purified by extraction, and finally they are crystallized.

It has been found, that it is preferred to use, as the substituted maleic anhydride, maleic anhydride, 3-methylmaleic anhydride and 3,4-dimethylmaleic anhydride and products, prepared by the Diels-Alder reaction of these compounds.

It has been further found that suitable primary amine is that which is linear, branched, cyclic or aromatic, wherein the number of —NH$_2$ groups on one molecule is 1 to 6.

It is preferred to use, as the organic solvent, toluene, ethylbenzene, xylene, chlorobenzene, decalin and mesitylene or mixtures thereof.

It is preferred to use, as the catalyst, betaine of the general formula

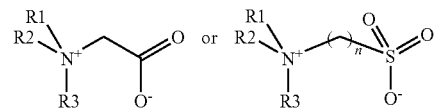

where R1, R2, R3 are the same or different alkyl groups with one to twenty four carbon atoms, or cycloalkyl groups with five to eight carbon atoms, or substituted phenyl groups bound to nitrogen through an aromatic nucleus, or substituted phenyl groups bound to nitrogen through a methyl-, ethyl-, propylradical, or a combination of the above groups.

As a catalyst, there may be further used betaine in a mixture with inorganic and organic acids, or betaine may be deposited on a solid carrier, or possibly, betaine is deposited on a carrier combined with inorganic acids, whereby the molar ratio of betaine to inorganic acid is 0-100.

It has been found that good results were achieved, when the inorganic acid was phosphoric acid or sulfuric acid, and the organic acid was methanesulfonic acid or p-toluenesulfonic acid or 4-ethylphenylsulfonic acid or benzenesulfonic acid or acetic acid or their halogen derivatives.

It is further preferred to use, as a carrier of betaine or betaine in combination with inorganic acids, silica gel, activated clay, diatomaceous earth, silicon dioxide, synthetic or natural aluminosilicates.

The advantages of betaine use in the maleimide preparation are:
- they cause minimum damage to the environment,
- they can be easily removed from the reaction medium by simple washing with water,
- they are easily available, they are commonly used as surfactants,
- the amount of organic and inorganic acids used is decreased or completely eliminated, thereby reducing demands on the construction of the production facilities with respect to corrosion.

EXAMPLES OF EMBODIMENTS OF THE INVENTION

Following examples explain in more detail, but do not limit the subject matter of the invention.

Example 1

A 3-necked 500 ml flask, equipped with a stirrer, azeotropic attachment and cooler, was charged with 90 g (0.454 mol) of 4,4'-diaminophenylmethane, 14.5 g of 30% aqueous solution of dimethyllaurylbetaine and 300 ml of ethylbenzene. This mixture was heated to the boiling point and water was distilled off the system. After water had been distilled off, the mixture was left to cool down to 110° C.

A 3-necked 1500 ml flask, equipped with a stirrer, column, thermometer, azeotropic attachment and cooler, was charged with 500 ml of ethylbenzene and 90 g (0.918 mol) of maleic anhydride. Hot ethylbenzene solution containing 90 g of 4,4'-diaminophenylmethane was gradually added to the solution so that the temperature of the future reaction mixture would not exceed 70° C. After adding ethylbenzene solution of methylenedianiline, the reaction mixture was stirred in a temperature range of 60 to 70° C. for another hour. The reaction mixture was heated to the reflux temperature. Arising water was trapped in the azeotropic attachment and after 7 hours the reaction water was distilled out. After the reaction mixture had been clarified, stirring was stopped. Insoluble fractions went to the bottom of the reaction vessel. The ethylbenzene solution was poured into a 1500 ml beaker. After cooling the solution down to 18° C. the arisen crystals of 4,4'-bis(maleimide)diphenylmethane (BMI) were sucked off. The yield was 104 g.

After thickening the mother liquor in a vacuum rotating evaporator another 8 g of BMI have been obtained. By extraction of insoluble residue with hot ethylbenzene still another 14.3 g of BMI have been obtained. Total yield of the reaction was 126.3 g (77.6%) BMI with the melting point of 160 to 162° C.

Example 2

A 3-necked 500 ml flask, equipped with a stirrer, azeotropic attachment and cooler, was charged with 20 g of maleic anhydride and 150 ml of toluene. 18 g (0.2 mol) of aniline and 1.06 g of triethylbetaine in 150 ml of toluene were added to this mixture at a temperature of 40° C. so that the temperature of the reaction mixture has not exceeded 70° C. Suspension of the respective maleamic acid and toluene, prepared in this way, was stirred at a temperature of 70° C. for another hour. The reaction mixture was heated to the reflux temperature. Arising reaction water was trapped in the azeotropic attachment and after 7 hours the reaction water was distilled out. After the reaction mixture had been clarified, stirring was stopped. Insoluble fractions in toluene went to the bottom of the reaction vessel. Clear toluene solution was poured into a 500 ml round-bottom flask. After thickening the toluene solution in a vacuum rotating evaporator 23 g (66.47%) of N-phenylmaleimide with the melting point of 84 to 86° C. have been obtained.

Example 3

A 3-necked 500 ml flask, equipped with a stirrer, azeotropic attachment and cooler, was charged with 22.54 g (0.23 mol) of maleic anhydride and 150 ml of toluene. 20 g (0.1 mol) of 4,4'-diaminodiphenylmethane and 13.6 g (0.1 mol) of trimethylbetaine in 150 ml of toluene were added to this mixture at a temperature of 40° C. so that the temperature of the reaction mixture has not exceeded 70° C. Suspension of the respective maleamic acid, prepared in this way, was stirred at a temperature of 70° C. for another hour. The reaction mixture was heated to the reflux temperature. Arising water was trapped in the azeotropic attachment and after 7 hours the reaction water was distilled out. After the reaction mixture had been clarified, stirring was stopped. Fractions insoluble in toluene went to the bottom of the reaction vessel. The hot toluene solution was poured into a 1000 ml three-necked flask. For the extraction of 4,4'-bis(maleimide)diphenylmethane (BMI) from insoluble residue 2×150 ml of toluene were added. The extraction was performed at a temperature of 105° C. After thickening the combined toluene solutions to 150 ml after cooling to 18° C. and filtering 27 g (75.41%) of BMI with the melting point of 159 to 161° C. have been obtained.

Example 4

A 3-necked 1500 ml flask, equipped with a stirrer, column, thermometer, azeotropic attachment and cooler, was charged with 750 ml of ethylbenzene and 80 g (0.81 mol) of maleic anhydride. 100 g (0.40 mol) of bis(2-aminophenyl)disulphide were gradually added to the solution at a temperature of 40° C. so that the temperature of the reaction mixture would not exceed 70° C. After adding the reaction mixture was stirred at a temperature of 65° C. for another hour. Then a mixture of dimethyllaurylbetaine with phosphoric acid, which was previously dried by azeotropic distilling off water present in the above catalyst, was added. The reaction mixture was heated to the reflux temperature. Arising water was trapped in the azeotropic attachment and after 16 hours the reaction water was distilled out. After the reaction mixture had been clarified, stirring was stopped. Insoluble fractions went to the bottom of the reaction vessel. The ethylbenzene solution was poured into a 1500 ml beaker. After cooling the solution down to 18° C. the arisen crystals of 4,4'-bis(maleimido)diphenyldisulphide (FMI) were sucked off. After drying from ethylbenzene they were washed with water. 133 g of FMI with the melting point of 161 to 163° C. were obtained.

After thickening the mother liquor in a vacuum rotating evaporator another 24.3 g of FMI have been obtained. The total yield of FMI was 95.6%.

INDUSTRIAL APPLICABILITY

Maleimides and their derivatives are widely applied in chemical industry as monomeric units for polyimides, which are characterized by high thermal endurance and dimensional stability. Some of the maleimide derivatives are used in rubber industry as antireversing agents and an agent improving rubber-metal adhesion.

The invention claimed is:

1. A method of preparation of maleimides, characterized in that it includes:
   a) reaction of a substituted maleic anhydride with a primary amine in an organic solvent in the presence of betaine at a temperature of 100 to 180° C., whereby the ratio of the primary amine to the substituted maleic anhydride is in the range of 0.6 to 1.6, and
   b) purification of maleimides by extraction and crystallization.

2. The method of claim 1 wherein the substituted maleic anhydride is maleic anhydride, 3-methyl maleic anhydride or 3,4-dimethylmaleic anhydride.

3. The method of claim 1 wherein the primary amine is linear, branched, cyclic or aromatic, and wherein the number of —$NH_2$ groups on one molecule is in the range of 1 to 6.

4. The method of claim 2 wherein the primary amine is linear, branched, cyclic or aromatic, and wherein the number of —$NH_2$ groups on one molecule is in the range of 1 to 6.

5. The method of claim 1 wherein the organic solvent is toluene, ethylbenzene, xylene, chlorobenzene, decalin or mesitylene or mixtures thereof.

6. The method of claim 1 wherein the molar ratio of betaine to the primary amine is in the range of 0.01 to 1.2.

7. The method of claim 2 wherein the molar ratio of betaine to the primary amine is in the range of 0.01 to 1.2.

8. The method of claim 1 wherein betaine has a general formula

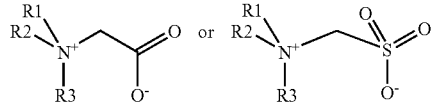

where R1, R2, R3 are the same or different alkyl groups with one to twenty-four carbon atoms, or cycloalkyl groups with five to eight carbon atoms, or substituted phenyl groups bound to nitrogen through an aromatic nucleus, or substituted phenyl groups bound to nitrogen through a methyl-, ethyl-, propylradical, or a combination of the above possibilities.

9. The method of claim 6 wherein betaine has a general formula

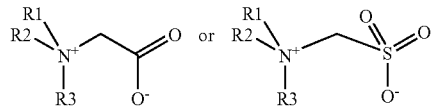

where R1, R2, R3 are the same or different alkyl groups with one to twenty-four carbon atoms, or cycloalkyl groups with five to eight carbon atoms, or substituted phenyl groups bound to nitrogen through an aromatic nucleus, or substituted phenyl groups bound to nitrogen through a methyl-, ethyl-, propylradical, or a combination of the above possibilities.

10. The method of claim 1 wherein as a catalyst, there is used betaine in a mixture with inorganic and organic acids, or it is deposited on a solid carrier, or it is deposited on a carrier in a combination with inorganic acids.

11. The method of claim 6 wherein as a catalyst, there is used betaine in a mixture with inorganic and organic acids, or it is deposited on a solid carrier, or it is deposited on a carrier in a combination with inorganic acids.

12. The method of claim 8 wherein as a catalyst, there is used betaine in a mixture with inorganic and organic acids, or it is deposited on a solid carrier, or it is deposited on a carrier in a combination with inorganic acids.

13. The method of claim 10 wherein the carrier used is silica gel, activated clay, diatomaceous earth, silicon dioxide, synthetic or natural aluminosilicates.

14. The method of claim 10 wherein the inorganic acid is phosphoric acid or sulfuric acid.

15. The method of claim 10 wherein the molar to molar ratio of betaine to inorganic acid is 0.01-100.

16. The method of claim 10 wherein the organic acid is methanesulfonic acid or p-toluenesulfonic acid or 4-ethylphenylsulfonic acid or benzenesulfonic acid.

* * * * *